United States Patent [19]

Steck et al.

[11] Patent Number: 4,967,013

[45] Date of Patent: Oct. 30, 1990

[54] PREPARATION OF HYDROXYBENZALDEHYDES

[75] Inventors: Werner Steck, Ludwigshafen; Helmut Lermer, Mannheim; Harald Rust, Neustadt; Gerhard Fritz, Dannstadt-Schauernheim; Hardo Siegel, Speyer, all of Fed. Rep. of Germany

[73] Assignee: BASF Aktiengesellschaft, Ludwigshaften, Fed. Rep. of Germany

[21] Appl. No.: 346,714

[22] Filed: May 3, 1989

[30] Foreign Application Priority Data

May 5, 1988 [DE] Fed. Rep. of Germany ....... 3815292

[51] Int. Cl.$^5$ ............................................. C07C 45/00
[52] U.S. Cl. .................................................. 568/433
[58] Field of Search ................................. 568/433, 805

[56]  References Cited
U.S. PATENT DOCUMENTS

| 4,273,941 | 6/1981 | Kawamura et al. | 564/416 |
| 4,473,713 | 9/1984 | Ratton | 568/805 |
| 4,667,037 | 5/1987 | Bryant III | 568/805 |
| 4,695,659 | 9/1987 | Andersson | 568/805 |

FOREIGN PATENT DOCUMENTS

| 2904315 | 8/1980 | Fed. Rep. of Germany . | |
| 56-166131 | 12/1981 | Japan | 568/433 |
| 139153 | 5/1920 | United Kingdom | 568/433 |

OTHER PUBLICATIONS

Chem. Abst., vol. 108, 1988—JP 62, 153,240.
Chem. Abst., vol. 107: JP-62 155,236.

*Primary Examiner*—Bruce Gray
*Attorney, Agent, or Firm*—Keil & Weinkauf

[57]  ABSTRACT

Hydroxybenzaldehydes of the formula (I) are prepared from a benzaldehyde of the formula (II) or its acetal, in which $R^1$ in the $R^1O$-phenyl ether group is an alkyl, cycloalkyl, alkylcycloalkyl or alkylaryl radical, $R^2$ is H or OH or is identical to $R^1$ and one or more $R^1O$-phenyl ether groups are ortho, meta or para to the aldehyde function, by a process in which a benzaldehyde of the formula (II) or its acetal, in which $R^1$ and $R^2$ have the abovementioned meanings and one or more $R^1O$-phenyl ether groups occupy the abovementioned position with respect to the aldehyde function, is converted into a hydroxybenzaldehyde of the formula (I) in the presence of water over a zeolite as a heterogeneous catalyst.

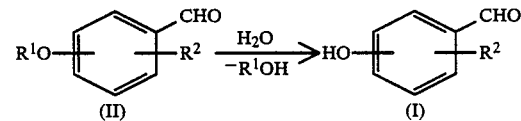

The catalysts used are, in particular, zeolites of the pentasil type.

12 Claims, No Drawings

PREPARATION OF HYDROXYBENZALDEHYDES

The present invention relates to a process for the preparation of hydroxybenzaldehydes by cleaving a phenol ether bridge in an aromatic aldehyde or its acetal in the presence of a zeolite catalyst.

A number of preparation methods have already been described for the synthesis of hydroxybenzaldehydes, which are useful intermediates for the preparation of drugs, such as antibiotics, agrochemicals, brightening agents for electrochemical metallization baths or dyes or are used as flavorings or components of synthetic scents.

The cleavage of phenol ethers which already have an aldehyde function on the phenol ring by acids or acid mixtures, for example of HBr in glacial acetic acid, bases, pyridinium chloride, Lewis acids, such as AlCl$_3$ or BCl$_3$, or reductive methods, such as hydrogenolysis, have been described in detail in Houben-Weyl, Methoden der organischen Chemie (1976), Volume 6/1, pages 314–390, etc.

The preparation of p-hydroxybenzaldehyde by treating a substituted benzaldehyde dialkyl acetal with aqueous hydrohalic acid is the subject of DE 29 04 315. This also gives a good overview of the prior art for the preparation of p-hydroxybenzaldehyde by various methods (column 1, lines 35–55). Thus, heating p-methoxybenzaldehyde with pyridinium chloride to 200° C.–220° C. is one method which gives p-hydroxybenzaldehyde (Ber. dtsch. Chem. Ges. 74 (1974), 1219). On the other hand, it is expressly pointed out that the treatment of p-methoxybenzaldehyde with HCl does not lead to p-hydroxybenzaldehyde, and treatment with HBr also makes possible only low yields. This is not surprising since aldehydes tend to undergo secondary reactions in the presence of mineral acids (column 2, lines 45–55).

Another multistage synthesis for p-hydroxybenzaldehyde is described in DE 28 39 053, where p-nitrotoluene is first converted into p-aminotoluene, and the latter is diazotized and then hydrolyzed to p-hydroxybenzaldehyde. Finally, J 6 2153 240 describes the oxidation of p-cresol to p-hydroxybenzaldehyde, while J 6 2155 236 describes a multistage preparation by acetoxylation, halogenation and hydrolysis.

Kirk-Othmer (Encyclopedia of Chemical Technology, Third Edition, Volume 13, pages 70–79) gives an overview of the preparation processes for salicylaldehyde or other hydroxybenzaldehydes. Many of the known preparation processes are multi-stage and therefore involved. These known processes are all carried out under homogeneous catalysis, for example in the presence of mineral acids. Thus, disadvantages such as the frequently difficult removal of the catalyst, or its loss, and sufficiently short contact times are not possible. In many cases, the permanent presence of the homogeneous catalyst or the fact that it cannot be separated off rapidly enough leads to secondary reactions which result in decomposition of the desired product or greatly reduce the yields. For example, 4-hydroxybenzaldehyde is unstable to acids and therefore cannot be obtained from anisaldehyde dialkyl acetal by homogeneous, acidic cleavage with hydrochloric acid (cf. DE 29 04 315, column 2, lines 45–55).

It is an object of the present invention to provide a preparation process for hydroxybenzaldehydes which employs heterogeneous catalysis and can be carried out in a technically simple manner.

We have found that this object is achieved and that, in the preparation of hydroxybenzaldehydes of the formula (I) from benzaldehydes of the formula (II) or their acetals, in which R$^1$ in the R$^1$O-phenyl ether group is an alkyl, cycloalkyl, alkylcycloalkyl or alkylaryl radical, R$^2$ is H or OH or is identical to R$^1$ and one or more R$^1$O-phenyl ether groups are ortho, meta or para to the aldehyde function, the abovementioned disadvantages of the known processes are avoided if a benzaldehyde of the formula (II) or its acetal, in which R$^1$ and R$^2$ have the abovementioned meanings and one or more R$^1$O-phenyl ether groups occupy the abovementioned position with respect to the aldehyde function, is converted into a hydroxybenzaldehyde of the formula (I) in the presence of water over a zeolite as a heterogeneous catalyst.

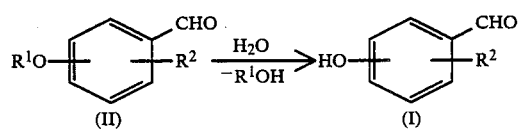

Monohydroxybenzaldehydes, such as para-, meta- or ortho-hydroxybenzaldehyde can be very readily obtained from the corresponding alkoxybenzaldehydes or their acetals if R$^1$ in the R$^1$O-phenyl ether group is alkyl, such as —CH$_3$ or tert-butyl and R$^2$ is H.

Particularly suitable catalysts are the zeolites of the pentasil type, for example the aluminosilicate zeolites, the borosilicate zeolites and the ferrosilicate zeolites, as well as gallium silicate zeolites. The novel process makes it possible to cleave phenol ethers which have one or more aldehyde functions on the phenyl nucleus by heterogeneous catalysis over a zeolite in a simple manner to give hydroxybenzaldehydes. For example, the industrially important 4- or 2-hydroxybenzaldehydes can readily be obtained in this manner from 4-methoxybenzaldehyde and 2-methoxybenzaldehyde or their dialkyl acetals. The disadvantages of the processes employing homogeneous catalysts, for example the expensive removal of the catalyst or the partial or complete decomposition of the end product by virtue of the fact that the homogeneous catalyst cannot be separated off sufficiently rapidly, are avoided. The novel process can be carried out by a continuous method and with short residence times and good yields. In the case of thermally unstable starting materials of the formula (II), this avoids or suppresses the undesirable thermal decarbonylation of the aldehyde function or isomerizations, which may take place as secondary reactions.

Starting materials of the formula (II) which are suitable for the novel process are, for example, monoalkoxybenzaldehydes, such as 4-methoxybenzaldehyde, 2-methoxybenzaldehyde, 3-methoxybenzaldehyde,4-ethoxybenzaldehyde, 4-tert-butoxybenzaldehyde [=4-(1,1-dimethylethoxy)-benzaldehyde] and 4-benzyloxybenzaldehyde [=4-(phenylmethoxy)-benzaldehyde] or monoalkoxyhydroxybenzaldehydes, for example 3-methoxy-4-hydroxybenzaldehyde, 3-hydroxy-4-methoxybenzaldehyde, and 2-hydroxy-3-ethoxybenzaldehyde, and dialkoxybenzaldehydes, for example 2,3-, 2,4- or 2,5- or 3,4- or 3,6-dimethoxybenzaldehyde. In the case of the benzaldehydes substituted by more than one alkoxy group, one or more alkoxy groups can be converted regioselectively to hydroxy groups, depending on the chemical nature of the starting materials or the envisaged object.

The dialkyl acetals, in particular the dimethyl acetals, of the stated aldehydes are also perfectly suitable.

Depending on the starting material, the reaction conditions which are suitable for the novel conversion in the gas phase reaction are 120° C.–370° C. and a space velocity WHSV of from 0.1 to 15 $h^{-1}$ (WHSV = g of starting mixture per g of catalyst per hour). The reaction can be carried out under atmospheric pressure in a fixed bed, fluid bed or fluidized bed.

It is advisable, depending on the reaction temperature and thermal stability of the substances, to reduce the time of contact of the reactants with the catalyst and/or to cool the reaction mixture rapidly after passage through the catalyst bed. In this way, it is possible to avoid or greatly suppress yield-reducing secondary reactions, for example decarbonylation reactions, even in the case of thermally unstable starting materials and/or end products.

The selectivity and the yields can be advantageously influenced even under reduced pressure, for example by means of a vacuum pump downstream of the discharge side of the catalyst bed, owing to the resulting short residence times over the catalyst, which may even be fractions of a second.

It is also possible to carry out the reaction in the liquid phase at from 120 to 300° C. and at a WHSV of from 0.1 to 15 $h^{-1}$. The reaction can be carried out under atmospheric pressure or under pressures from atmospheric pressure to 40 bar, depending on the volatility of the starting compounds.

The procedure is preferably carried out continuously, and a recycled gas procedure with complete or partial recycling of the reactor discharge may be appropriate.

Sparingly volatile, liquid or solid starting materials are advantageously used in dissolved or emulsified form, for example in alcohols, tetrahydrofuran, toluene or petroleum ether. In general, dilution of all starting materials, including the more readily volatile solvents, or, in the gas phase, dilution with inert gases, such as $N_2$, Ar, He or steam, is possible. In the case of a liquid starting material of the formula (II), for example 4-methoxybenzaldehyde, after the addition of water a finely dispersed emulsion of the water in the methoxybenzaldehyde can often be obtained simply by stirring. This emulsion can then be fed by means of suitable metering pumps, in the desired amount, directly to the reactor and converted there.

The end products discharged frequently consist of two phases when water is used, so that excess water or water formed by secondary reactions can readily be separated off from the organic phase. In the presence of alcohols, such as methanol, or of mixtures of starting material, water and solvents, either homogeneous mixtures or, as described above, pumpable and meterable emulsions are obtained.

Where dialkyl acetals of the starting materials (II), for example 2- or 4-methoxybenzaldehyde dimethyl acetals, are used, they can be passed as such or in solution in the solvent over the zeolite catalyst bed, in the presence of water.

In other cases, it is advantageous to carry out a two-stage process by first converting the diacetals of the alkoxybenzaldehydes completely or partially into the corresponding alkoxybenzaldehydes over an acidic, heterogeneous catalyst in the presence of water and then further converting the aldehyde-containing reacted mixture into hydroxybenzaldehydes in the same reactor or in another reactor.

After the reaction, the products are isolated from the discharged mixture by a conventional method, for example by distillation, extraction or freezing out from the reaction mixture; unconverted starting materials are, if required, recycled to the reaction. If the hydroxybenzaldehydes have sufficiently acidic hydroxyl groups, for example 4-hydroxybenzaldehyde, these hydroxybenzaldehydes can be readily separated by means of a two-phase mixture of toluene and aqueous sodium hydroxide solution, since the methoxybenzaldehyde accumulates in the toluene whereas the hydroxybenzaldehyde accumulates in the sodium hydroxide solution. After neutralization of the aqueous, alkaline fraction and removal of the water, the hydroxybenzaldehyde can readily be separated off from the solid residue using a solvent, such as methanol.

The catalysts used for the novel process are zeolites. Zeolites are crystalline aluminosilicates which have a highly ordered structure with a three-dimensional network of $SiO_4$ or $AlO_4$ tetrahedra which are bonded by common oxygen atoms. The ratio of Si and Al atoms to oxygen is 1 : 2. The electrovalency of the aluminum-containing tetrahedra is balanced by the inclusion of cations in the crystal, for example an alkali metal ion or hydrogen ion. Cation exchange is possible. The voids between the tetrahedra are occupied by water molecules prior to dehydration by drying or calcination.

In the zeolites, instead of aluminum other elements, such as B, Ga, Fe, Cr, V, As, Sb or Be, can be incorporated in the framework, or the silicon can be replaced by a tetravalent element, such as Ge, Ti, Zr or Hf.

Depending on their structure, the zeolites are divided into different groups. For example, the zeolite structure is formed by chains of tetrahedra in the mordenite group and by sheets of tetrahedra in the chabasite group, whereas in the faujasite group the tetrahedra are arranged to form polyhedra, for example in the form of a cubooctahedron which consists of 4-membered rings and 6membered rings. Depending on the bonding of the cubooctahedra, which results in cavities and pores of different sizes, a distinction is made between zeolites of type A, L, X or Y.

Zeolites of the pentasil type are particularly suitable for the novel process. These have a 5-membered ring consisting of $SiO_4$ tetrahedra as a basic building block. They have a characteristic high $SiO_2/Al_2O_3$ ratio, also referred to as a modulus, and pore sizes which are between those of the zeolites of type A and those of type X or Y. For example, pentasil zeolites having $SiO_2/Al_2O_3$ ratios of from 15 to 700 have proven highly suitable for the novel process. The preparation of these pentasil zeolites is described in, inter alia, U.S. Pat. No. 3,702,886. The preparation of the similar borosilicate zeolites of type AMS-1B is the subject of DE 27 46 790.

The zeolites which can be used according to the invention can have different chemical compositions; for example, aluminosilicate, borosilicate, ferrosilicate, beryllium silicate, gallium silicate, chromium silicate, arsenosilicate, antimony silicate and bismuth silicate zeolites or mixtures of these, and aluminogermanate, borogermanate, gallium germanate and iron germanate zeolites or mixtures of these are suitable. The aluminosilicate, borosilicate and ferrosilicate zeolites of the pentasil type are particularly suitable for the novel process. The aluminosilicate zeolite is prepared, for example, from an aluminum compound, preferably Al(OH)$_3$ or Al$_2$(SO$_4$)$_3$, and a silicon component, preferably finely divided silica, in aqueous amine solution, in particular in polyamines, such as 1,6-diaminohexane or 1,3-diaminopropane or triethylenetetramine solution, with or, in particular, without the addition of an alkali or alkaline earth, at from 100 to 220° C. under autogenous pressure. Isotactic zeolites according to European Patent No. 0,034,727 are also suitable. The aluminosilicate zeolites obtained have an SiO$_2$/Al$_2$O$_3$ ratio of from 10 to 40,000, depending on the choice of the amounts of starting materials.

These aluminosilicate zeolites can be synthesized in an ether medium, such as diethylene glycol dimethyl ether, in an alcoholic medium, such as methanol or 1,4-butanediol, or in water.

The borosilicate zeolite is synthesized, for example, at from 90 to 200° C. under autogenous pressure by reacting a boron compound, eg. H$_3$BO$_3$, with a silicon compound, preferably finely divided silica, in aqueous amine solution, in particular in a solution of 1,6-diaminohexane or 1,3-diaminopropane or triethylenetetramine, with or, in particular, without the addition of an alkali or an alkaline earth. Isotactic borosilicate zeolites according to European Patent No. 0,034,727 can also be used. It is also possible to employ borosilicate zeolites which are crystallized not from an aqueous amine solution but from an ether solution, eg. diethylene glycol dimethyl ether, or from an alcoholic solution, eg. 1,6-hexanediol. The preparation of the boron zeolite is described in, for example, European Patent No. 0,007,081.

The ferrosilicate zeolite is obtained, for example, from an iron compound, preferably Fe$_2$(SO$_4$)$_3$, and a silicon compound, preferably finely divided silica, in aqueous amine solution, in particular 1,6-diaminohexane, with or without the addition of an alkali or alkaline earth, at from 100 to 200° C. under autogenous pressure. The preparation is described in DE 28 31 611.

The suitable silicon-rich zeolites (SiO$_2$/Al$_2$O$_3$ greater than or equal to 10) also include the known ZSM types and ferrierite (European Patent No. 0,012,473) and NU-1 (U.S. Pat. No. 4,060,590) as well as Silicalite ® (U.S. Pat. No. 4,061,724).

The aluminosilicate, borosilicate and ferrosilicate zeolites thus prepared can be isolated, dried at from 100 to 160° C. and calcined at from 450 to 550° C. and then molded with a binder in a weight ratio of zeolite to binder of from 90 : 10 to 40 : 60 to give extrudates or pellets. Suitable binders are various aluminas, preferably boehmite, amorphous aluminosilicates having an SiO$_2$/ Al$_2$O$_3$ ratio of from 25 : 75 to 90 : 5, SiO$_2$, TiO$_2$, mixtures of finely divided SiO$_2$ and finely divided Al$_2$O$_3$, and clay. After the molding procedure, the extrudates or pellets are dried at 110° C. for 16 h and calcined at 500° C. for 16 h.

Suitable catalysts are also obtained if the aluminosilicate or borosilicate zeolite isolated is molded directly after drying and is not subjected to calcination until after the molding procedure. The aluminosilicate and borosilicate zeolites can be used in pure form, without a binder, as extrudates or pellets, and, for example, ethylcellulose, stearic acid, potato starch, formic acid, oxalic acid, acetic acid, nitric acid, ammonia, amines, silicoesters or graphite or a mixture of these can be used as extrusion assistants or peptizing assistants.

If, because of its method of preparation, the zeolite is not in the caralytically active, acidic H form but, for example, in the Na form, the latter can be converted completely or partially into the desired H form by ion exchange, for example with ammonium ions, and subsequent calcination or by treatment with acids.

If, when the zeolite catalysts are used, deactivation due to coking occurs, it is advisable to regenerate the zeolites by burning off the coke deposit with air or with an air/N$_2$ mixture at from 400 to 550° C., preferably 500° C. The zeolites thus in general regain their initial activity.

By controlled precoking, it is also possible to adjust the activity of the catalyst for optimum selectivity of the desired reaction product.

In order to achieve very high selectivity, high conversion and long catalyst lives, it is advantageous to modify the zeolites, the content of the modifying elements being such that sufficient activity of the catalysts is ensured.

In a suitable method of modifying the catalysts, for example, the unmolded or molded zeolite is doped with metal salts by ion exchange or by impregnation. The metals used are alkali metals, such as Li, K or Cs, alkaline earth metals, such as Mg, Ca or Ba, earth metals, such as B, Al or Ga, transition metals, such as Cu, Zn, Cr, Mn, Fe, Co, Ni, W or Mo, and rare earth metals, such as Ce, La, Pr or Nd.

Modification with phosphorus by treatment with phosphoric acids or phosphoric esters such as trimethyl phosphate is also possible.

Advantageously, doping is carried out in such a way that the molded zeolite is initially taken in a riser tube and, for example, an aqueous or ammoniacal solution of a halide or of a nitrate of the metals described above is passed over the said zeolite at from 20 to 100° C. Ion exchange of this type can be carried out, for example, for the hydrogen, ammonium or alkali metal form of the zeolite. In another possible method of applying the metals to the zeolite, the zeolite material is impregnated with a halide, a nitrate, a carbonate or an oxide of the metals described above, in aqueous, alcoholic or ammoniacal solution. Both ion exchange and impregnation are followed by one or more drying steps and, if required, repeated calcination.

In a possible embodiment, for example, magnesium acetate is dissolved in water. This solution is used to impregnate the molded or unmolded zeolite for about 30 minutes. The supernatant solution is freed from water in a rotary evaporator. Thereafter, the impregnated zeolite is dried at about 130° C. and calcined at 500° C. This impregnation process can be carried out several times in succession in order to obtain the desired metal content.

Ion exchange of the zeolite in the H form or ammonium form or alkali metal form can be carried out by a procedure in which the zeolite, in the form of extrudates or pellets, is initially taken in a column and an aqueous solution of ammonium chloride is circulated over the said zeolite at a slightly elevated temperature of from 30 to 80° C. for from 15 to 20 h. The product is then washed thoroughly with water, dried at about 110° C. and calcined at about 500° C.

In another possible method of modification, the molded or unmolded zeolite material is subjected to a treatment with acids, such as hydrochloric acid, hydrofluoric acid and phosphoric acid, and/or steam. Advantageously, zeolites in powder form are treated with 1 N phosphoric acid for 1 h at 80° C. After the treatment, the product is washed with water, dried at 100° C. for 16 h and calcined at 500° C. for 20 h.

In another procedure, zeolites, before or after they have been molded with binders, are treated with a 3-25, in particular 12-20, % strength by weight aqueous hydrochloric acid, for example for from 1 to 3 h at from 60 to 80° C. The zeolite thus treated is then washed with water, dried, and calcined at from 400 to 500° C.

In a particular embodiment of the acid treatment, the zeolite material, before being molded, is treated at elevated temperatures with 0.001-2 N, preferably 0.05-0.5 N, hydrofluoric acid, for example by refluxing for from 0.5 to 5 h, preferably from 1 to 3 h.

After the zeolite material has been isolated, for example by filtering it off and washing it thoroughly, it is advantageously dried at from 100 to 160° C. and calcined at from 450 to 600° C.

In another preferred embodiment of the acid treatment, the zeolite material is molded with a binder and then treated at from 50 to 90° C. for from 1 to 3 h with 3-25, preferably 12-20, % strength by weight hydrochloric acid. The zeolite material is then washed thoroughly, dried at from 100 to 160° C. and calcined at from 450 to 600° C. Subsequent treatment with HF and HCl may also be advantageous.

In another procedure, zeolites can be modified by applying phosphorus compounds, such as triethyl phosphate or primary, secondary or tertiary sodium phosphate. The treatment with primary sodium phosphate has proven particularly advantageous. Here, the zeolites in the form of extrudates, pellets or fluidized material, are impregnated with aqueous $NaH_2PO_4$ solution, dried at 110° C. and calcined at 500° C.

The catalysts described here can be used alternatively as 2-4 mm extrudates, as pellets of 3-5 mm diameter or as chips having particle sizes of from 0.1 to 0.5 mm or as fluidized material. Experiments in the gas phase The reaction in the gas phase is carried out under isothermal conditions in a tube reactor (coil, 0.6 cm internal diameter, 90 cm length) for several hours over a fixed-bed catalyst. The amount of catalyst is varied from 1 to 10 g, corresponding to a space velocity WHSV of from 10 to 0.5 $h^{-1}$. The reaction products are isolated by conventional methods and characterized by GC/MS, NMR, the melting point or the boiling point. Quantitative determination of the reaction products and of the starting materials is carried out by gas chromatograpy or by weighing the fractions obtained by distillation or extraction.

EXPERIMENTS IN THE LIQUID PHASE

In the tube reactor described above, pressure control valves and safety valves are installed at suitable points. The starting materials in the form of a solution or emulsion are metered in this case using a commercial high pressure pump.

PREPARATION OF THE CATALYSTS

Catalyst 1:

A ferrosilicate zeolite of the pentasil type is prepared under hydrothermal conditions, under autogenous pressure and at 165° C. from 273 g of a sodium waterglass (27.2 of $SiO_2$ and 8.5% of $Na_2O$), 126 g of 1,6-diaminohexane, 551 g of water, 20.6 g of 96% strength sulfuric acid and 31.1 g of iron(III) sulfate in a stirred autoclave. The crystalline reaction product is filtered off, washed thoroughly, dried at 110° C. for 24 h and then calcined at 500° C. for 24 h. This ferrosilicate zeolite is composed of 84.5% by weight of $SiO_2$, 12.1% by weight of $Fe_2O_3$ and 0.074% by weight of Na. This material is molded with a molding assistant to give 4 mm extrudates, which are dried at 110° C. for 16 h and calcined at 500° C. for 24 h.

The extrudates are subjected to ion exchange 4 times with 20% strength by weight $NH_4Cl$ solution (15 ml of solution/g of moldings) at 80° C. in a riser tube. They are then washed chloride-free. The extrudates are dried at 110° C. for 10 h and then calcined at 500° C. for 5 h. The Na content is now 0.015% by weight.

Catalyst 2:

An aluminosilicate zeolite of the ZSM-5 type is prepared under hydrothermal conditions, under autogenous pressure and at 175° C., from 1.0 kg of pyrogenic silica, 48.0 g of sodium aluminate (58.6% by weight of $Al_2O_3$ and 40.0% by weight of $Na_2O$), 44.0 g of sodium hydroxide, 1.69 kg of aqueous tetra-n-propylammonium hydroxide solution (20% strength) and 16.6 kg of water in a stirred autoclave. The crystalline reaction product is filtered off, washed thoroughly and dried at 110° C. for 24 h and calcined at 500° C. for 24 h. This zeolite is characterized by the following composition: 85.9% by weight of $SiO_2$, 2.3% by weight of $Al_2O_3$ and 0.32% by weight of Na.

This zeolite is molded with a molding assistant to give 2 mm extrudates. These are dried at 110° C. for 16 h and calcined at 500° C. for 16 h.

The extrudates are subjected to ion exchange four times with 20% strength by weight $NH_4Cl$ solution (15 ml solution/g of moldings) at 80° C. in a riser tube. They are then washed chloride-free. The extrudates are dried at 110° C. for 10 h and then calcined at 500° C. for 5 h. The Na content is now 0.007% by weight.

Catalyst 3:

A borosilicate zeolite of the ZSM-5 type is prepared under hydrothermal conditions, under autogenous pressure and at 165° C., from 6.0 kg of silicasol (30% by weight of $SiO_2$), 118 g of boric acid, 252 g of sodium hydroxide, 1.44 kg of tetra-n-propylammonium bromide and 14.7 kg of water in a stirred autoclave. The crystalline reaction product is filtered off, washed thoroughly, dried at 110° C. for 24 h and calcined at 500° C. for 24 h. This zeolite is characterized by the following composition: 86.3% by weight of $SiO_2$, 1.38% by weight of $B_2O_3$ and 0.65% by weight of Na.

This zeolite is molded with a molding assistant to give 2 mm extrudates. These are dried at 110° C. for 16 h and calcined at 500° C. for 16 h.

The extrudates are subjected to ion exchange four times with 20% strength by weight $NH_4Cl$ solution (15 ml solution/g of moldings) at 80° C. in a riser tube. They are then washed chloride-free. The extrudates are dried at 110° C. for 10 h and then calcined at 500° C. for 5 h. The Na content is now 0.015% by weight.

Catalyst 4:

An aluminosilicate zeolite of the ZSM-5 type is prepared under hydrothermal conditions, under autogenous pressure and at 170° C., from 13.2 kg of silicasol (30% by weight of $SiO_2$), which, owing to its origin, contains traces of aluminum, 314 g of sodium hydroxide, 3.36 kg of aqueous tetra-n-propylammonium hydroxide solution (20% strength) and 6.4 kg of water in a stirred autoclave. The crystalline reaction product is filtered off, washed thoroughly, dried at 110° C. for 24 h and calcined at 500° C. for 24 h. This zeolite is characterized by the following composition: 81.4% by weight of $SiO_2$, 0.20% by weight of $Al_2O_3$ and 1.0% by weight of Na.

This zeolite is molded with a molding assistant to give 2 mm extrudates. These are dried at 110° C. for 16 h and calcined at 500° C. for 16 h.

The extrudates are subjected to ion exchange four times with 20% strength by weight NH$_4$Cl solution (15 ml of solution/g of moldings) at 80° C. in a riser tube. They are then washed chloride-free. The extrudates are dried at 110° C for 10 h and then calcined at 500° C. for 5 h. The Na content is now 0.02% by weight.

Catalyst 5:

The aluminosilicate zeolite obtained as catalyst 4 is molded with pyrogenic silica (8 parts by weight : 2 parts by weight) and a molding assistant to give 2 mm extrudates, which are dried at 110° C. for 16 h and calcined at 500° C. for 16 h.

The extrudates are subjected to ion exchange four times with 20% strength by weight NH$_4$Cl solution (15 ml of solution/g of moldings) at 80° C. in a riser tube. They are then washed chloride-free. The extrudates are dried at 110° C. for 10 h and then calcined at 500° C. for 5 h. The Na content is now 0.018% by weight.

Catalyst 6:

The borosilicate zeolite of the pentasil type is prepared in a hydrothermal synthesis from 650 g of finely divided SiO$_2$, 373 g of H$_3$BO$_3$ and 8,000 g of an aqueous 1,6-diaminohexane solution (50% by weight of amine) at 165° C. under autogenous pressure in a stirred autoclave. The crystalline reaction product is filtered off, washed thoroughly, dried at 100° C. for 24 h and calcined at 500° C. for 24 h. This borosilicate zeolite is composed of 95.4% by weight of SiO$_2$ and 3.31% by weight of B$_2$O$_3$.

This material is molded with a molding assistant to give 2 mm extrudates, which are dried at 110° C. for 16 h and calcined at 500° C. for 16 h.

Catalyst 7:

An aluminosilicate zeolite of the pentasil type is prepared under hydrothermal conditions, under autogenous pressure and at 150° C., from 650 g of finely divided SiO$_2$ and 203 g of Al$_2$(SO$_4$)$_3$·18H$_2$O in 11.3 kg of an aqueous 1,6-diaminohexane solution (42% by weight of amine) in a stirred autoclave. The crystalline reaction product is filtered off, washed thoroughly, dried at 110° C. for 24 h and calcined at 500° C. for 24 h. This aluminosilicate zeolite contains 92.6% by weight of SiO$_2$ and 4.6% by weight of Al$_2$O$_3$.

This material is molded with a molding assistant to give 2 mm extrudates, which are dried at 110° C. for 16 h and calcined at 500° C. for 16 h.

Catalyst 8:

Catalyst 8 is a commercial Al$_2$O$_3$ (D 10–10 ®).

Catalyst 9:

Catalyst 9 is a commercial SiO$_2$ (D 11–10 ®).

Catalyst 10:

A borosilicate zeolite obtained as catalyst 3 is molded with pyrogenic silica 8 parts by weight : 2 parts by weight) and a molding assistant to give 2 mm extrudates, which are dried at 110° C. for 16 h and calcined at 500° C. for 16 h.

The extrudates are subjected to ion exchange four times with 20% strength by weight NH$_4$Cl solution (15 ml of solution/g of moldings) at 80° C. in a riser tube. They are then washed chloride-free. The extrudates are dried at 110° C. for 10 h and then calcined at 500° C. for 5 h. The Na content is now 0.02% by weight.

Catalyst 11:

The borosilicate zeolite of the pentasil type is prepared in a hydrothermal synthesis from 740 g of finely divided SiO$_2$, 360 g of H$_3$BO$_3$, and 9.7 kg of an aqueous 1,6-diaminohexane solution (50% by weight of amine) at 165° C. under autogenous pressure in a stirred autoclave. The crystalline reaction product is filtered off, washed thoroughly, dried at 160° C. for 24 h and calcined at 500° C. for 24 h. This borosilicate zeolite is composed of 92.9% by weight of SiO$_2$ and 2.92% by weight of B$_2$O$_3$.

The borosilicate zeolite is refluxed with 0.08 N HF (3.6 g of HF solution/g of zeolite) for 1 h. The zeolite is then filtered off, washed, dried at 110° C. and calcined at 500° C. for 5 h.

The treated borosilicate zeolite is molded with an amorphous aluminosilicate (weight ratio of SiO$_2$ to Al$_2$O$_3$=75 : 25) in a weight ratio of 60 : 40 with the addition of a molding assistant to give 2 mm extrudates, which are dried at 110° C. for 16 h and then calcined at 500° C. for 16 h.

The F content of the catalyst is 0.055% by weight.

Catalyst 12:

An aluminosilicate zeolite of the pentasil type is prepared under hydrothermal conditions, under autogenous pressure and at 150° C., from 650 g of finely divided SiO$_2$, 203 g of Al$_2$(SO$_4$)$_3$·18H$_2$O in 11.9 kg of an aqueous 1,6-diaminohexane solution (46% by weight of amine) in a stirred autoclave. The crystalline reaction product is filtered off, washed thoroughly, dried at 110° C. for 24 h and calcined at 500° C. for 24 h. This aluminosilicate zeolite contains 89.5% by weight of SiO$_2$ and 2.7% by weight of Al$_2$O$_3$.

This material is molded with a molding assistant to give 2 mm extrudates, which are dried at 110° C. for 16 h and calcined at 500° C. for 16 h.

The extrudates are impregnated with an aqueous Mg(OOC—CH$_3$)$_2$·4H$_2$O solution, dried at 130° C. for 2 h and calcined at 540° C. for 2 h. The Mg content is 2.0% by weight.

Catalyst 13:

The borosilicate zeolite of catalyst 11 is molded with a molding assistant to give 2 mm extrudates, which are dried at 110° C. and calcined at 500° C. for 16 h.

The extrudates are impregnated with trimethyl phosphate, dissolved in water, for 30 minutes. The P content after drying at 110° C. for 2 h is 1.73% by weight.

Catalyst 14:

The borosilicate zeolite of the pentasil type is prepared in a hydrothermal synthesis from 552 g of finely divided SiO$_2$, 331 g of H$_3$BO$_3$ and 10.5 kg of an aqueous triethylenetetramine solution (47% by weight of amine) at 75° C. under autogenous pressure in a stirred autoclave. The crystalline reaction product is filtered off, washed thoroughly, dried at 140° C. for 24 h and calcined at 500° C. for 24 h. This borosilicate zeolite is composed of 88.0% by weight of SiO$_2$ and 5.23% by weight of B$_2$O$_3$.

This material is molded with a molding assistant to give 2 mm extrudates, which are dried at 110° C. for 16 h and calcined at 500° C. for 16 h.

Catalyst 15:

The borosilicate zeolite of catalyst 11 is molded with a molding assistant to give 2 mm extrudates, which are dried at 110° C. for 16 h and calcined at 500° C. for 16 h.

The extrudates are impregnated with an aqueous Mg(OOC—CH$_3$)$_2$·4H$_2$O solution, as for catalyst 12. The Mg content is 1.1% by weight.

Catalyst 16:

The borosilicate zeolite extrudates prepared in the case of catalyst 6 are impregnated with La(NO$_3$)$_3$·6H$_2$O solution, as for catalyst 12 (La=1.8% by weight).

Catalyst 17:

The borosilicate zeolite prepared as catalyst 11 is extruded with pseudoboehmite in a weight ratio of 60:40, and the extrudates are dried at 110° C. for 16 h and calcined at 500° C. for 16 h. The extrudates are impregnated with Cr(NO$_3$)$_3$·9H$_2$O solution, as for catalyst 12 (Cr=1.90% by weight).

EXAMPLES 1 TO 20

Gas phase reaction for the preparation of 4-hydroxybenzaldehyde (I) from 4-methoxybenzaldehyde (II)

Starting material A: Mixture of 4-methoxybenzaldehyde (anisaldehyde), methanol and water in a molar ratio of 1 : 1.5 : 1.5

The tube reactor described above is fed continuously under atmospheric pressure, by means of a metering pump, with 10 ml/h of the starting material A, an inert atmosphere being provided at the same time by means of a stream of nitrogen. The gaseous educts and reaction products flow through the catalyst bed from bottom to top. After the reaction in the gas phase over the catalyst, the selected space velocity WHSV in h$^{-1}$, the reaction temperature in the catalyst bed in [° C.] and the catalyst used are listed in Table 1, the reacted mixture is condensed in a glass apparatus and, after the time-on-stream stated in hours [h], the reacted mixture is analyzed by gas chromatography ((I) = 4-hydroxybenzaldehyde; (II) = 4-methoxybenzaldehyde; byproducts: anisole (=III) and phenol (=IV)). The conversions and selectivities are given in percentages by area.

TABLE 1

| | | | | | GC analysis of the reacted mixture | | | | |
|---|---|---|---|---|---|---|---|---|---|
| Example | Catalyst | WHSV h$^{-1}$ | N$_2$ (Nl/h.) | Time onstream (h) | Temp. (°C.) | Conversion of (II) (%) | Amount of (I) (% by area) | Selec. in (%) | | |
| | | | | | | | | (I) | (III) | (IV) |
| 001 | 1 | 1.4 | 5.0 | 8 | 270 | 46.0 | 17.8 | 38.6 | 36.4 | 25.1 |
| | 1 | 1.4 | 5.0 | 28 | 270 | 28.2 | 15.5 | 55.1 | 27.7 | 17.3 |
| 002 | 2 | 1.4 | 5.0 | 6 | 270 | 20.4 | 10.0 | 53.4 | 34.4 | 10.2 |
| 003 | 3 | 1.4 | 5.0 | 7 | 270 | 37.1 | 17.3 | 46.5 | 33.4 | 20.1 |
| | 3 | 1.4 | 5.0 | 31 | 270 | 24.0 | 15.4 | 64.3 | 24.3 | 11.3 |
| 004 | 4 | 1.4 | 5.0 | 2 | 210 | 4.1 | 3.5 | 84.8 | 7.1 | 0.0 |
| 005 | 4 | 1.4 | 5.0 | 2 | 240 | 32.2 | 16.4 | 51.5 | 30.5 | 18.0 |
| 006 | 4 | 1.4 | 5.0 | 8 | 270 | 31.3 | 16.4 | 52.6 | 30.5 | 16.9 |
| 007 | 4 | 1.4 | 5.0 | 28 | 270 | 22.1 | 13.9 | 62.7 | 23.0 | 11.8 |
| 008 | 4 | 1.4 | 5.0 | 14 | 350 | 50.2 | 5.7 | 11.3 | 54.5 | 25.8 |
| 009 | 4 | 1.4 | 50.0 | 4 | 270 | 29.4 | 11.7 | 39.9 | 38.3 | 21.7 |
| 010 | 4 | 2.8 | 50.0 | 4 | 270 | 21.5 | 5.2 | 24.1 | 42.3 | 33.5 |
| 011 | 4 | 10.0 | 50.0 | 4 | 270 | 10.2 | 5.3 | 52.4 | 38.2 | 9.1 |
| 012 | 5 | 1.4 | 5.0 | 27 | 270 | 19.3 | 13.2 | 68.7 | 21.4 | 9.9 |
| 013 | 6 | 1.4 | 5.0 | 7 | 270 | 10.9 | 9.1 | 83.5 | 11.1 | 0.0 |
| 014 | 6 | 1.4 | 5.0 | 23 | 270 | 10.1 | 9.2 | 90.5 | 9.8 | 0.0 |
| 015 | 6 | 1.4 | 5.0 | 75 | 270 | 10.4 | 8.8 | 85.1 | 6.5 | 0.0 |
| 016 | 6R | 1.4 | 5.0 | 23 | 270 | 10.0 | 8.9 | 88.7 | 11.1 | 0.0 |
| | R = Regenerated catalyst of Example 15 | | | | | | | | | |
| 017 | 12 | 1.4 | 5.0 | 2 | 270 | 13.4 | 7.1 | 53.0 | 29.7 | 13.1 |
| 018 | 13 | 1.4 | 5.0 | 2 | 270 | 9.5 | 4.4 | 46.3 | 13.6 | 15.6 |
| 019 | 8 | 1.4 | 5.0 | 6 | 270 | 2.9 | 0.0 | 0.0 | 0.0 | 0.3 |
| 020 | 9 | 1.4 | 5.0 | 7 | 270 | 0.9 | 0.0 | 0.0 | 0.0 | 0.0 |

COMPARATIVE EXAMPLES 21 and 22

4-Hydroxybenzaldehyde from 4-methoxybenzaldehyde without the addition of water

Starting material B: solution of 1 mole of 4-methoxybenzaldehyde (II) and 3 moles of methanol The reactions are carried out in the same way as in Example 1. However, no water is added. The results are shown in Table 2.

TABLE 2

| COMPARATIVE EXAMPLES WITHOUT THE ADDITION OF WATER | | | | | | | | | | |
|---|---|---|---|---|---|---|---|---|---|---|
| | | | | | | GC analysis of the reacted mixture | | | | |
| Example | Catalyst | WHSV h$^{-1}$ | N$_2$ (Nl/h) | Time onstream (h) | Temp. (°C.) | Conversion of (II) (%) | Amount of (I) (% by area) | Selec. in (%) | | |
| | | | | | | | | (I) | (III) | (IV) |
| 021 | 4 | 1.4 | 5.0 | 6 | 350 | 28.5 | 5.5 | 19.3 | 51.7 | 13.3 |
| 022 | 4 | 1.4 | 5.0 | 6 | 270 | 2.1 | 1.5 | 72.5 | 27.5 | 0.0 |

EXAMPLES 23 TO 42

4-Hydroxybenzaldehyde from 4-methoxybenzaldehyde

Starting material C: emulsion of 4-methoxybenzaldehyde and water in a molar ratio of 1 : 1

The reactions are carried out in a manner similar to Examples 1 to 19. However, water is added but no methanol. The starting material and reaction product and the blanketing stream of nitrogen are passed downward over the fixed-bed catalyst by the co-current method. With the aid of this downward-flow procedure, it is also possible to convert liquid phases. At 200° C., for example, the water will be in the form of steam but p-methoxybenzaldehyde (boiling point 248° C.) will still be substantially in the form of a liquid. In this case too, the desired p-hydroxybenzaldehyde is obtained.

TABLE 3

| Example | Catalyst | WHSV $h^{-1}$ | $N_2$ (Nl/h) | Time onstream (h) | Temp. (°C.) | Conversion of (II) (%) | Amount of (I) (% by area) | Selec. in (%) (I) | (III) | (IV) |
|---|---|---|---|---|---|---|---|---|---|---|
| 23 | 4 | 1.4 | 5.0 | 15 | 250 | 23.4 | 15.6 | 61.5 | 22.3 | 2.6 |
| 24 | 4 | 2.8 | 5.0 | 15 | 250 | 21.2 | 11.5 | 54.2 | 11.5 | 7.0 |
| 25 | 4 | 1.4 | 5.0 | 4 | 350 | 43.6 | 12.5 | 28.6 | 36.1 | 25.3 |
| 26 | 5 | 1.4 | 5.0 | 15 | 250 | 22.6 | 12.3 | 54.5 | 14.6 | 8.3 |
| 27 | 3 | 1.4 | 5.0 | 15 | 250 | 33.4 | 19.0 | 57.0 | 23.6 | 18.4 |
| 28 | 10 | 1.4 | 5.0 | 15 | 250 | 28.5 | 14.0 | 49.0 | 18.7 | 12.3 |
| 29 | 10R | 1.4 | 5.0 | 15 | 250 | 24.4 | 14.0 | 57.4 | 21.6 | 20.9 |
| R = regenerated catalyst of Example 28 |
| 30 | 10 | 10.0 | 5.0 | 15 | 250 | 23.2 | 8.9 | 38.3 | 35.7 | 26.0 |
| 31 | 1 | 1.4 | 5.0 | 7 | 250 | 40.5 | 19.8 | 48.9 | 20.0 | 15.6 |
| 32 | 6 | 1.4 | 5.0 | 25 | 250 | 14.1 | 13.5 | 95.5 | 4.5 | 0.0 |
| 33 | 6 | 1.4 | 5.0 | 7 | 250 | 10.0 | 10.0 | 100 | 0.0 | 0.0 |
| 34 | 6 | 1.4 | 5.0 | 31 | 250 | 28.6 | 25.7 | 89.8 | 4.4 | 0.0 |
| Product of Example 32 passed twice more over the catalyst bed |
| 35 | 10 | 1.4 | 5.0 | 7 | 250 | 12.2 | 8.9 | 73.2 | 12.0 | 8.1 |
| 36 | 2 | 1.4 | 5.0 | 7 | 350 | 32.6 | 6.7 | 20.6 | 46.6 | 20.6 |
| 37 | 14 | 1.4 | 5.0 | 2 | 250 | 11.2 | 10.4 | 92.6 | 7.5 | 0.0 |
| 38 | 15 | 1.4 | 5.0 | 4 | 250 | 7.0 | 6.2 | 88.2 | 6.8 | 5.0 |
| 39 | 16 | 1.4 | 5.0 | 4 | 250 | 9.7 | 9.0 | 93.2 | 6.9 | 0.0 |
| 40 | 17 | 1.4 | 5.0 | 7 | 250 | 13.8 | 9.6 | 69.5 | 17.9 | 9.4 |
| 41 | 8 | 1.4 | 5.0 | 7 | 250 | 1.4 | 0.7 | 51.8 | 0.0 | 0.0 |
| 42 | 9 | 1.4 | 5.0 | 7 | 250 | 0.0 | 0.0 | 00.0 | 0.0 | 0.0 |

EXAMPLE 43

4-Hydroxybenzaldehyde (I) from 4-tert-butoxybenzaldehyde (II)

Starting material D: Emulsion of 4-tert-butoxybenzaldehyde and water in a molar ratio of 1:1

The reaction is carried out in a similar manner to Example 23, using the downward-flow procedure.

TABLE 4

| Example | Catalyst | WHSV $h^{-1}$ | $N_2$ (Nl/h) | Time onstream (h) | Temp. (°C.) | Conversion of (II) (%) | Amount of (I) (% by area) | Selec. in (%) (I) | (III) |
|---|---|---|---|---|---|---|---|---|---|
| 43 | 6 | 1.4 | 5.0 | 2 | 150 | 100.0 | 100.0 | 100 | 00.0 |

EXAMPLE 44

4-Hydroxybenzaldehyde (I) from 4-benzyloxybenzaldehyde (II)

Starting material E: Solution of 4-benzyloxybenzaldehyde, methanol and water in a molar ratio of 0.1 : 12 : 2.5

The reactions are carried out in a similar manner to Example 23, using the downward-flow procedure.

TABLE 5

| Example | Catalyst | WHSV $h^{-1}$ | $N_2$ (Nl/h) | Time onstream (h) | Temp. (°C.) | Conversion of (II) (%) | Amount of (I) (% by area) | Selec. in (%) (I) | (III) |
|---|---|---|---|---|---|---|---|---|---|
| 44 | 3 | 1.4 | 5.0 | 6 | 250 | 100.0 | 22.6 | 22.6 | 27.7 |

EXAMPLES 45 TO 49

LIQUID-PHASE REACTIONS UNDER PRESSURE

Starting material A: Emulsion of 4-methoxybenzaldehyde, methanol and water in a molar ratio of 1 : 1.5 : 1.5
Starting material C: Emulsion of 4-methoxybenzaldehyde and water in a molar ratio of 1 : 1

The starting materials are introduced into the modified tube reactor using a commercial high pressure metering pump. The pressure in the reactor is controlled by means of pressure control valves on the product discharge side. To ensure a uniform procedure, the operating pressure of the pump on the feed side is always 1–2 bar above that of the pressure control system on the discharge side, which system is adjusted to, for example, 15–20 bar.

TABLE 6

| Example | Catalyst | WHSV $h^{-1}$ | Starting material | Time onstream (h) | Temp. (°C.) | Conversion of (II) (%) | Amount of (I) (% by area) | Selec. in (%) (I) | (III) | (IV) |
|---|---|---|---|---|---|---|---|---|---|---|
| 045 | 6 | 1.4 | A | 7 | 250 | 11.3 | 10.7 | 94.3 | 5.6 | 0.0 |
| 046 | 1 | 1.4 | C | 4 | 240 | 28.6 | 20.3 | 70.9 | 15.8 | 13.2 |
| 047 | 6 | 1.4 | C | 6 | 240 | 14.4 | 13.1 | 90.8 | 3.9 | 3.1 |
| 048 | 3 | 1.4 | C | 10 | 240 | 31.4 | 21.7 | 69.2 | 14.0 | 14.3 |

TABLE 6-continued

| Example | Catalyst | WHSV h$^{-1}$ | Starting material | Time onstream (h) | Temp. (°C.) | Conversion of (II) (%) | Amount of (I) (% by area) | Selec. in (%) (I) | (III) | (IV) |
|---|---|---|---|---|---|---|---|---|---|---|
| 049 | 4 | 1.4 | C | 6 | 240 | 24.2 | 13.2 | 54.4 | 3.9 | 4.7 |

EXAMPLES 50 TO 57

2-Hydroxybenzaldehyde (I) from 2-methoxybenzaldehyde (II)

Starting material G: Emulsion of 2-methoxybenzaldehyde and water in a molar ratio of 1 : 2
Starting material H: Mixture of 2-methoxybenzaldehyde, methanol and water in a molar ratio of 1 : 1.5 : 1.5
Starting material I: Emulsion of 2-methoxybenzaldehyde dimethyl acetal and water in a molar ratio of 1 : 2.

The reactions are carried out similarly to Example 1, as gas phase reactions.

TABLE 7

| Example | Catalyst | WHSV h$^{-1}$ | Starting material | Time onstream (h) | Temp. (°C.) | Conversion of (II) (%) | Amount of (I) (% by area) | Selec. in (%) (I) | (III) | (IV) |
|---|---|---|---|---|---|---|---|---|---|---|
| 050 | 1 | 1.4 | I | 2 | 250 | 43.9 | 30.8 | 70.1 | 13.8 | 13.2 |
| 051 | 1 | 1.4 | G | 4 | 240 | 76.7 | 27.9 | 36.4 | 24.3 | 38.4 |
| 052 | 1 | 1.4 | G | 2 | 300 | 90.1 | 9.2 | 10.1 | 30.4 | 45.0 |
| 053 | 7 | 0.7 | G | 6 | 250 | 58.4 | 41.6 | 71.3 | 18.2 | 30.6 |
| 054 | 7 | 1.4 | G | 6 | 250 | 36.1 | 28.2 | 78.1 | 8.9 | 9.5 |
| 055 | 7 | 1.4 | H | 2 | 250 | 82.7 | 58.4 | 70.6 | 12.5 | 9.4 |
| 056 | 7 | 1.4 | H | 2 | 250 | 63.8 | 31.6 | 49.6 | 16.1 | 29.4 |
|  |  |  |  | 29 | 250 | 26.4 | 22.1 | 84.0 | 9.1 | 6.4 |
| 057 | 7 | 1.4 | I | 2 | 250 | 66.1 | 35.7 | 54.0 | 12.1 | 22.5 |

EXAMPLES 58 TO 63

2-Hydroxybenzaldehyde (I) from 2-methoxybenzaldehyde (II)

Starting material H: Mixture of 2-methoxybenzaldehyde, methanol and water in a molar ratio of 1 : 1.5 : 1.5
Starting material K: Emulsion of 2-methoxybenzaldehyde and water in a molar ratio of 1 : 1
Starting material L: Mixture of 2-methoxybenzaldehyde dimethyl acetal, methanol and water in a molar ratio of 1.5 : 1.5

The reactions are carried out similarly to Example 45, as a liquid phase reaction under superatmospheric pressure of from 16 to 18 bar.

TABLE 8

| Example | Catalyst | WHSV h$^{-1}$ | Starting material | Time onstream (h) | Temp. (°C.) | Conversion of (II) (%) | Amount of (I) (% by area) | Selec. in (%) (I) | (III) | (IV) |
|---|---|---|---|---|---|---|---|---|---|---|
| 058 | 1 | 1.4 | H | 1 | 240 | 8.6 | 5.9 | 68.9 | 14.4 | 0.0 |
| 059 | 1 | 1.4 | H | 6 | 240 | 16.3 | 14.1 | 86.2 | 9.2 | 0.0 |
| 060 | 1 | 1.4 | K | 1 | 240 | 53.3 | 32.9 | 61.6 | 29.5 | 4.7 |
| 061 | 1 | 1.4 | K | 6 | 240 | 11.5 | 9.7 | 84.4 | 9.1 | 0.0 |
| 062 | 1 | 1.4 | L | 1 | 240 | 55.9 | 39.9 | 71.4 | 18.2 | 0.0 |
| 063 | 1 | 1.4 | L | 2 | 240 | 28.0 | 23.6 | 84.2 | 12.3 | 0.0 |

EXAMPLES 64 AND 65

3-Hydroxybenzaldehyde (I) from 3-methoxybenzaldehyde (II)

GAS PHASE REACTION CORRESPONDING TO EXAMPLE 23

Starting material M: Emulsion of 3-methoxybenzaldehyde and water in a molar ratio of 1 : 2

TABLE 9

| Example | Catalyst | WHSV h$^{-1}$ | Starting material | Time onstream (h) | Temp. (°C.) | Conversion of (II) (%) | Amount of (I) (% by area) | Selec. in (%) (I) | (III) | (IV) |
|---|---|---|---|---|---|---|---|---|---|---|
| 064 | 1 | 1.4 | M | 4 | 250 | 56.0 | 54.9 | 98.1 | 0.0 | 0.0 |
| 065 | 7 | 1.4 | M | 4 | 250 | 55.9 | 54.3 | 97.1 | 0.0 | 0.0 |

We claim:

1. A process for the preparation of a hydroxybenzaldehyde of the formula (I) from a benzaldehyde of the formula (II) or its acetal, in which $R^1$ in the $R^1O$-phenyl ether group is an alkyl, cycloalkyl, alkylcycloalkyl or alkylaryl radical, $R^2$ is H or OH or is identical to $R^1$ and one or more $R^1O$-phenyl ether groups are ortho, meta or para to the aldehyde function, wherein a benzaldehyde of the formula (II) or its acetal, in which $R^1$ and $R^2$ have the abovementioned meanings and one or more $R^1O$-phenyl ether groups occupy the abovementioned position with respect to the aldehyde function, is converted into a hydroxybenzaldehyde of the formula (I) in the presence of water over a zeolite as a heterogeneous catalyst.

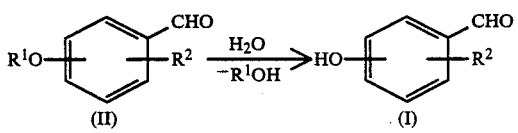

2. A process for the preparation of a monohydroxybenzaldehyde as claimed in claim 1 from a benzaldehyde or its acetal in which $R^1$ in the $R^1O$-phenyl ether group is an alkyl or alkylaryl radical, $R^2$ is H and the $R^1O$-phenyl ether group is ortho, meta or para to the aldehyde function, wherein a benzaldehyde of the formula (II) or its acetal, in which $R^1$ and $R^2$ have the abovementioned meanings and the $R^1O$-phenyl ether group occupies the abovementioned position with respect to the aldehyde function, is converted into a hydroxybenzaldehyde of the formula (I) in the presence of water over a zeolite as a heterogeneous catalyst.

3. A process as claimed in claim 1, wherein the catalyst used is a zeolite of the pentasil type.

4. A process as claimed in claim 1, wherein the catalyst used is an aluminosilicate zeolite.

5. A process as claimed in claim 1, wherein the catalyst used is a borosilicate zeolite.

6. A process as claimed in claim 1, wherein the catalyst used is a.

7. A process as claimed in claim 3, wherein the catalyst used is a zeolite doped with an alkali metal and/or an alkaline earth metal.

8. A process as claimed in claim 3, wherein the catalyst used is a zeolite doped with transition metals.

9. A process as claimed in claim 3, wherein the catalyst used is a zeolite doped with rare earth metals.

10. A process as claimed in claim 3, wherein the catalyst used is a zeolite treated with acids.

11. A process as claimed in claim 3, wherein the catalyst used is a zeolite doped with phosphorus.

12. A process as claimed in claim 3, wherein the catalyst used is a doped zeolite which additionally contains phosphorus.

* * * * *